(12) United States Patent
Denison (10) Patent No.: US 7,803,179 B2
(45) Date of Patent: Sep. 28, 2010

(54) INTRAVASCULAR STENTS

(75) Inventor: Andy E. Denison, Temecula, CA (US)

(73) Assignee: Abbott Vascular Solutions Inc., Santa Clara, CA (US)

( * ) Notice: Subject to any disclaimer, the term of this patent is extended or adjusted under 35 U.S.C. 154(b) by 2310 days.

(21) Appl. No.: 10/158,362

(22) Filed: May 30, 2002

(65) Prior Publication Data

US 2003/0225449 A1    Dec. 4, 2003

(51) Int. Cl.
 *A61F 2/06* (2006.01)
(52) U.S. Cl. .................... 623/1.15; 623/1.2
(58) Field of Classification Search ............... 623/1.15, 623/1.2, 1.16
See application file for complete search history.

(56) References Cited

U.S. PATENT DOCUMENTS

| 5,690,644 | A  | 11/1997 | Yurek et al. |
| 5,735,893 | A  | 4/1998  | Lau et al. |
| 5,938,697 | A  | 8/1999  | Killion et al. |
| 6,171,334 | B1 | 1/2001  | Cox |
| 6,179,867 | B1 | 1/2001  | Cox |
| 6,273,910 | B1 | 8/2001  | Limon |
| 6,273,911 | B1 | 8/2001  | Cox et al. |
| 6,312,459 | B1 | 11/2001 | Huang et al. |
| 6,375,676 | B1 | 4/2002  | Cox |
| 6,380,457 | B1 | 4/2002  | Yurek et al. |
| 6,511,505 | B2 | 1/2003  | Cox et al. |
| 6,537,311 | B1 | 3/2003  | Cox et al. |
| 6,652,579 | B1 | 11/2003 | Cox et al. |
| 6,695,862 | B2 | 2/2004  | Cox et al. |
| 6,709,454 | B1 | 3/2004  | Cox et al. |
| 6,755,855 | B2 | 6/2004  | Yurek et al. |

FOREIGN PATENT DOCUMENTS

WO    WO 99/15108 A    4/1999

*Primary Examiner*—Todd E Manahan
*Assistant Examiner*—Jonathan A Hollm
(74) *Attorney, Agent, or Firm*—Fulwider Patton LLP (57) ABSTRACT

Stent designs for use in vessels, such as the carotid and coronary arteries, are disclosed. The stents consist of a plurality of radially expandable cylindrical elements generally aligned on a common longitudinal stent axis and interconnected by one or more interconnecting members placed so that the stent is flexible in a longitudinal direction. The cylindrical elements form a generally serpentine wave pattern transverse to the longitudinal axis between alternating valley portions and peak portions. The interconnecting members are attached to the double-curved portions to connect a cylindrical element to an adjacent cylindrical element and interconnecting members are attached to the inverted double-curved portions to connect the cylindrical element to the other adjacent cylindrical element. The stent designs include both a six crown and an eight crown stent which exhibit flexibility and sufficient radial strength to support the vessel.

52 Claims, 6 Drawing Sheets

INTRAVASCULAR STENTS

BACKGROUND OF THE INVENTION

The present invention relates to expandable endoprosthesis devices, generally called stents, which are adapted to be implanted into a patient's body lumen, such as a blood vessel, to maintain the patency thereof. Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis.

Stents are generally cylindrically-shaped devices which function to hold open and sometimes expand a segment of a blood vessel or other arterial lumen, such as coronary artery. Stents are usually delivered in a compressed condition to the target site and then deployed at that location into an expanded condition to support the vessel and help maintain it in an open position. They are particularly suitable for use to support and hold back a dissected arterial lining which can occlude the fluid passageway there through.

A variety of devices are known in the art for use as stents and have included coiled wires in a variety of patterns that are expanded after being placed intraluminally on a balloon catheter; helically wound coiled springs manufactured from an expandable heat sensitive metal; and self-expanding stents inserted into a compressed state for deployment into a body lumen. One of the difficulties encountered in using prior art stents involve maintaining the radial rigidity needed to hold open a body lumen while at the same time maintaining the longitudinal flexibility of the stent to facilitate its delivery and accommodate the often tortuous path of the body lumen.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from shape memory metals or super-elastic nickel-titanium (NiTi) alloys, which will automatically expand from a compressed state when the stent is advanced out of the distal end of the delivery catheter into the blood vessel. Such stents manufactured from expandable heat sensitive materials allow for phase transformations of the material to occur, resulting in the expansion and contraction of the stent.

Expandable stents are delivered to the target site by delivery systems which often use balloon catheters as the means for delivering and expanding the stent in the target area. One such stent delivery system is disclosed in U.S. Pat. No. 5,158,548 to Lau et al. Such a stent delivery system has an expandable stent in a contracted condition placed on an expandable member, such as an inflatable balloon, disposed on the distal portion of an elongated catheter body. A guide wire extends through an inner lumen within the elongated catheter body and out its distal end. A tubular protective sheath is secured by its distal end to the portion of the guide wire which extends out of the distal end of the catheter body and fits over the stent mounted on the expandable member on the distal end of the catheter body.

Some prior art stent delivery systems for implanting self-expanding stents include an inner lumen upon which the compressed or collapsed stent is mounted and an outer restraining sheath which is initially placed over the compressed stent prior to deployment. When the stent is to be deployed in the body vessel, the outer sheath is moved in relation to the inner lumen to "uncover" the compressed stent, allowing the stent to move to its expanded condition into the target area.

In many procedures which utilize stents to maintain the patency of the patient's body lumen, the size of the body lumen can be quite small which prevents the use of some commercial stents which have profiles which are entirely too large to reach the small vessel. In particular, often in PTCA procedures, the stenosis is located in the very distal regions of the coronary arteries which often have small diameters. Many of these distal lesions are located deep within the tortuous vasculature of the patient which requires the stent to not only have a small profile, but also high flexibility to be advanced into these regions. As a result, the stent must be sufficiently flexible along its longitudinal axis, yet be configured to expand radially to provide sufficient strength and stability to maintain the patency of the body lumen. Since many commercial stents lack both the low profile and extreme flexibility needed to reach such distal lesions, they are not available for utilization for such procedures.

What has been needed is a stent which has a low profile and a high degree of flexibility so that it can be advanced through tortuous passage ways of the anatomy and can be expanded within the body vessel to maintain the patency of the vessel. Additionally, the expanded stent must have adequate structural strength (hoop strength) to hold the body lumen open once expanded. Such a stent should also have sufficient radio-paque properties to permit it to be sufficiently visualized on external monitoring equipment, such as a fluoroscope, to allow the physician to place the stent in the exact target location. The present invention satisfies these and other needs.

SUMMARY OF THE INVENTION

The present invention is directed to stents which can be used in body vessels, such as the carotid arteries and other peripheral arteries, along with the coronary arteries. The stents of the present invention are intended, but are not limited, to the effective treatment of diseased vessels having diameters from about 3.0 to 26.0 millimeters.

The stents of the present invention can be formed from super elastic nickel titanium alloys, or other shape memory materials, which allow the stent to be self expandable. Alternatively, the stent designs of the present invention could be used in conjunction with balloon expandable stents made from stainless steel or other conventional stent materials.

In all embodiments, the stents of the present invention have sufficient longitudinal flexibility along their longitudinal axis to facilitate delivery through tortuous body lumens, yet remain stable when expanded radially to maintain the patency of a body lumen, such as an artery or other vessel, when implanted therein. The present invention particularly relates to unique strut patterns which have a high degree of longitudinal flexibility and conformability, while providing sufficient radial-expansibility and strength to hold open the body lumens. The high radial strength possessed by the stents of the present invention allow them to be used in treating calcified lesions.

Generally, the greater the longitudinal flexibility of the stents, the easier and the more safely they can be delivered to the implantation site, particularly where the implantation site is on a curved section of a body lumen, such as a coronary artery or peripheral blood vessel, and especially in saphenous veins and larger vessels. The designs of the present invention have sufficient flexibility to conform to the patient's vasculature, thus preventing vessel straightening by the stent. Moreover, the stents of the present invention are crush proof, making them particularly suitable for implantation in the carotid arteries.

Each of the different embodiments of the stents of the present invention include a plurality of adjacent cylindrical elements (often referred to as "rings") which are generally expandable in the radial direction and arranged in alignment along a longitudinal stent axis. The cylindrical elements are formed in a variety of serpentine wave patterns transverse to the longitudinal axis and contain a plurality of alternating peaks and valleys. At least one interconnecting member (sometimes referred to as a "spine") extends between adjacent cylindrical elements and connects them to one another. These interconnecting members, selectively positioned throughout the stent, ensure minimal longitudinal contraction during radial expansion of the stent in the body vessel. The serpentine patterns have varying degrees of curvature in the regions of peaks and valleys and are adapted so that radial expansion of the cylindrical elements are generally uniform around their circumferences during expansion of the stent from the collapsed position to the expanded position.

The stents of the present invention also have strut patterns which enhance the strength of the ends of the stent and the overall radiopacity of the stent, yet retain high longitudinal flexibility along their longitudinal axis to facilitate delivery through tortuous body lumens and remain stable when expanded radially to maintain the patency of the body lumen.

The resulting stent structures are a series of radially expandable cylindrical elements that are spaced longitudinally close enough so that small dissections in the wall of a body lumen may be pressed back into position against the luminal wall, but not so close as to compromise the longitudinal flexibility of the stent both when negotiating through the body lumens in their unexpanded state and when expanded into position within the vessel. The design of the stents contribute to form small gaps between struts to minimize tissue prolapse. Each of the individual cylindrical elements may rotate slightly relative to their adjacent cylindrical elements without significant deformation, cumulatively providing stents which are flexible along their length and about their longitudinal axis, but which still are very stable in their radial direction in order to resist collapse after expansion.

In one embodiment of the present invention, each cylindrical element of the stent includes six peak portions (often referred to as "crowns") and six valley portions which provide sufficient coverage of the vessel when placed in the expanded or deployed position. In this design, each cylindrical element consists of an alternating pattern of valley portions, including double-curved (W) portions and Y-shaped portions, and peak portions, including alternating, inverted double-curved portions and Y-shaped portions. The plurality of interconnecting members extend between adjacent cylindrical elements and connect adjacent cylindrical elements to one another. In particular, interconnecting members are connected both axially and circumferentially to three alternating double-curved portions to connect a cylindrical element to three Y-shaped portions of an adjacent cylindrical element, and interconnecting members are connected both axially and circumferentially to three alternating, inverted double-curved portions to connect a cylindrical element to three alternating, inverted Y-shaped portions of an adjacent cylindrical element. This particular alignment of interconnecting members provides adequate flexibility to the stent and also helps prevent foreshortening of the stent as it expands radially outward. In addition, the particular placement of the interconnecting links within the valley portions of each double-curved portion is designed to increase axial stiffness and help reduce the protrusion of the Y-shaped portions from the circumference of the stent. Further, the discontinuing pattern of interconnecting members results in a highly flexible stent that does not kink upon bending. Both the distal and proximal ends of this stent design can be entirely composed of "W" patterns which provide additional strength to the ends of the stent. The resulting stent provides sufficient coverage for vessel scaffolding while maintaining excellent flexibility to reach distal lesions and possessing sufficient radial strength to hold the target vessel open. An alternative pattern using eight crowns and eight discontinuous interconnecting members also can be utilized and will exhibit these same physical properties.

The serpentine pattern of the individual cylindrical elements are in phase with each other in order to reduce the contraction of the stent along their length when expanded. In these embodiments of the present invention, interconnecting members align behind each other in an alternating fashion to create a discontinuous "spine" which extends from one end of the stent to the other. Specifically, alternating rows of interconnecting members are preferably used to connect adjacent cylindrical elements, with the exception, however, at end of the stent wherein at least two continuous rows of interconnecting members form one continuous spine. This particular construction also helps prevent the stent from foreshortening when expanded.

In another embodiment of the invention, a plurality of adjacent cylindrical elements alternate between two similar patterns of six valley portions and six peak portions throughout the body of the stent. The interconnecting members of each alternating, inverted double-curved portion within each cylindrical element form a continuous spine extending from one end of the stent to the other. Each pattern consists of six valley portions, namely six double-curved portions and six peak portions, namely three inverted double-curved portions and three inverted Y-shaped portions. Moreover, each of the cylindrical elements are connected to an adjacent cylindrical element by three interconnecting members. The plurality of cylindrical elements are located at both ends of the stent which have an alternating pattern of inverted double-curved portions and Y-shaped portions on one end and a pattern of alternating double-curved portions and inverted Y-shaped portions on the opposite end of the stent.

In yet another embodiment of the invention, a plurality of adjacent cylindrical elements of the stent includes a plurality of alternating valley portions, namely alternating Y-shaped portions and double-curved portions, and peak portions, namely alternating, inverted Y-shaped portions and inverted double-curved portions. A plurality of interconnecting members extend between the adjacent cylindrical elements and connecting adjacent cylindrical elements to one another and interconnecting members of each double-curved portion within each cylindrical element form a continuous spine extending from one end of the stent to the other. Each of the cylindrical elements include six peak portions and six valley portions. The six peak portions include three inverted Y-shaped portions and three inverted double-curved portions, and the six valley portions include three Y-shaped portions and three double-curved portions. The stent further includes cylindrical elements located at both ends of the stent which have a pattern of alternating, inverted double-curved portions and Y-shaped portions on one end and a pattern of alternating, double-curved portions and inverted Y-shaped portions on the opposite end of the stent.

A stent made in accordance with the present invention can be readily delivered to the desired target location by mounting it on a stent delivery catheter which includes a retractable sheath, or other means, to hold the stent in its collapsed position prior to deployment.

The present invention also provides a method for making a longitudinally flexible stent for implanting in a body lumen and expandable from a contracted condition to an expanded condition. In this embodiment, a plurality of adjacent cylindrical elements are provided such that each cylindrical element has a circumference extending around a longitudinal stent axis and is substantially independently expandable in the radial direction. The plurality of adjacent cylindrical elements are arranged in alignment along the longitudinal stent axis. A serpentine wave pattern is formed transverse to the longitudinal axis that contains a plurality of alternating valley portions and peak portions, the valley portions including alternating double-curved portions and Y-shaped portions, and the peak portions including alternating, inverted double-curved portions and Y-shaped portions. A plurality of interconnecting members are provided to connect adjacent cylindrical elements to one another. In forming the serpentine wave pattern, the double-curved and Y-shaped valley portions of one cylindrical element are nested within an adjacent cylindrical element by arranging the serpentine patterns in phase with each other.

Other features and advantages of the present invention will become more apparent from the following detailed description of the invention when taken in conjunction with the accompanying exemplary drawings.

DETAILED DESCRIPTION OF THE PREFERRED EMBODIMENTS

Prior art stent designs, such as the MultiLink Stent™ manufactured by Advanced Cardiovascular Systems, Inc., Santa Clara, Calif., include a plurality of cylindrical rings that are connected by three connecting members between adjacent cylindrical rings. Each of the cylindrical rings is formed of a repeating pattern of U-, Y-, and W-shaped members, typically having three repeating patterns forming each cylindrical element or ring. A more detailed discussion of the configuration of the MultiLink Stent™ can be found in U.S. Pat. No. 5,569,295 (Lam) and U.S. Pat. No. 5,514,154 (Lau et al.).

Figure 1:
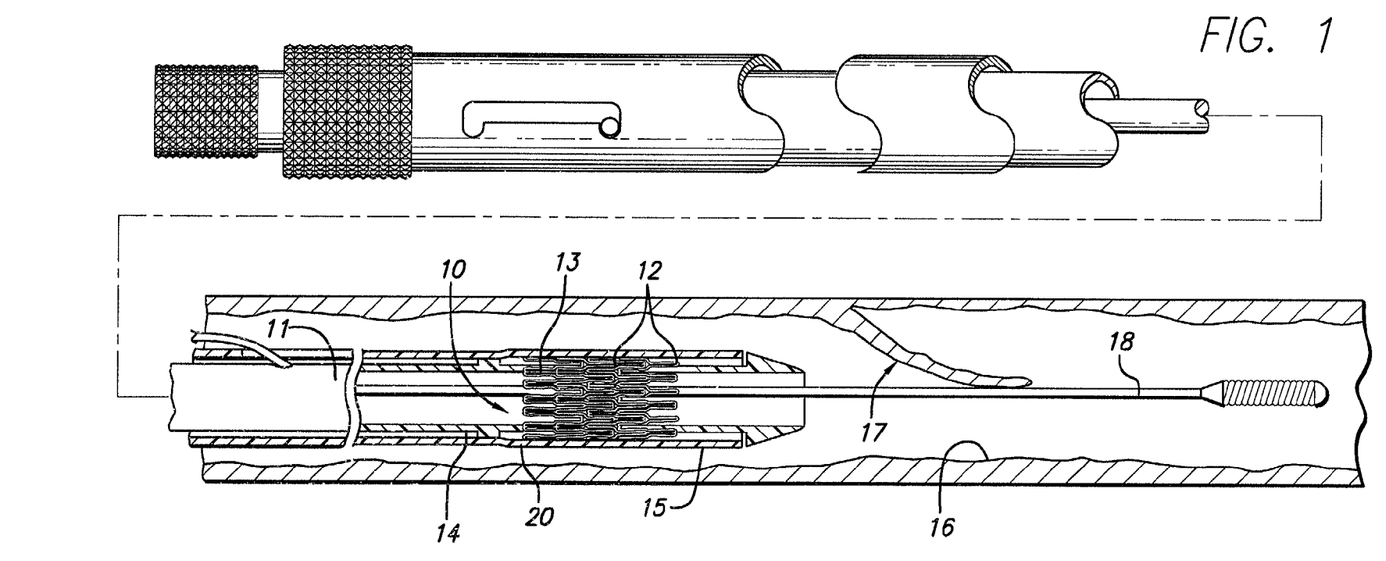
FIG. 1 is an elevational view, partially in section, depicting the stent embodying features of the present invention mounted on a delivery catheter disposed within a body vessel.
Figure 4:
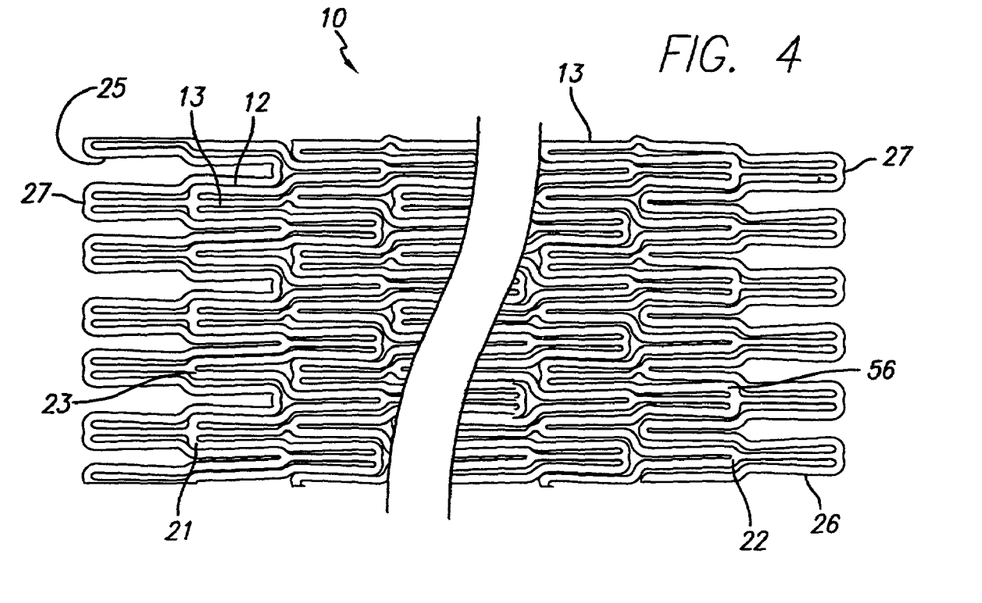
FIG. 4 is a plan view of one particular embodiment of a flattened stent of the present invention, which illustrates the serpentine pattern including peaks and valleys which form the cylindrical elements of the stent and permit the stent to achieve a small crimp profile, yet is expandable to a larger diameter to maintain the patency of a small vessel.

Beyond those prior art stents, FIG. 1 illustrates an exemplary embodiment of stent 10 incorporating features of the present invention, which stent is mounted onto delivery catheter 11. FIG. 4 is a plan view of this exemplary embodiment stent 10 with the structure flattened out into two dimensions to facilitate explanation. Stent 10 generally comprises a plurality of radially expandable cylindrical elements 12 disposed generally coaxially and interconnected by interconnecting members 13 disposed between adjacent cylindrical elements 12. The delivery catheter 11 has an inner tubular member 14 upon which the collapsed stent 10 is mounted. A restraining sheath 15 extends over both the inner tubular member 14 and stent 10 in a co-axial relationship. The stent delivery catheter 11 is used to position the stent 10 within an artery 16 or other vessel. The artery 16, as shown in FIG. 1, has a dissected or detached lining 17 which has occluded a portion of the arterial passageway.

Figure 2:
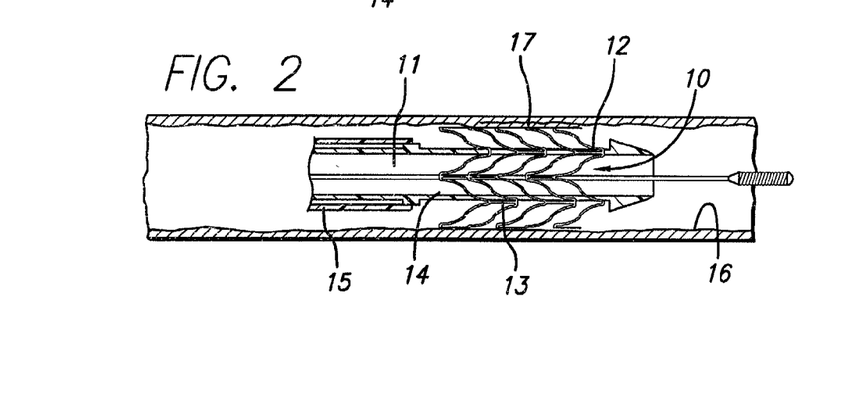
FIG. 2 is an elevational view, partially in section, similar to that shown in FIG. 1, wherein the stent is expanded within a vessel, pressing the lining against the vessel wall.

In one particular embodiment, the delivery of the stent 10 is accomplished in the following manner. Stent 10 is first mounted onto the delivery catheter 11 with the restraining sheath placed over the collapsed stent. The catheter-stent assembly can be introduced within the patient's vasculature in a conventional Seldinger technique through a guiding catheter (not shown). A guide wire 18 is disposed through the damaged arterial section with the detached or dissected lining 17. The catheter-stent assembly is then advanced over guide wire 18 within artery 16 until the stent 10 is directly under the detached lining 17. The restraining sheath 15 is retracted exposing the stent 10 and allowing it to expand against the inside of artery 16, which is illustrated in FIG. 2. While not shown in the drawing, artery 16 is preferably expanded slightly by the expansion of stent 10 to seat or otherwise embed stent 10 to prevent movement. Indeed, in some circumstances during the treatment of stenotic portions of an artery, the artery may have to be expanded considerably in order to facilitate passage of blood or other fluid therethrough.

Figure 3:
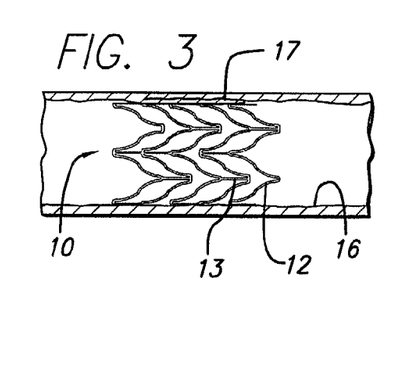
FIG. 3 is an elevational view, partially in section, showing the expanded stent within the body vessel after withdrawal of the delivery catheter.

While FIGS. 1-3 depict a vessel having detached lining 17, stent 10 can be used for purposes other than repairing the lining. Those other purposes include, for example, supporting the vessel, reducing the likelihood of restenosis, or assisting in the attachment of a vascular graft (not shown) when repairing an aortic abdominal aneurysm. The delivery catheter 11 is configured to advance through the patient's vascular system by advancing over a guide wire by any of the well known methods of an over the wire (OTW) system (not shown) or a well known rapid exchange (RX) catheter system, such as the one shown in FIG. 1.

In general, stent 10 serves to hold open the artery 16 after catheter 11 is withdrawn, as illustrated in FIG. 3. Due to the formation of stent 10, the undulating component of the cylindrical elements of stent 10 is relatively flat in a transverse cross-section so that when stent 10 is expanded, cylindrical elements 12 are pressed into the wall of artery 16 and as a result do not interfere with the blood flow through artery 16. Cylindrical elements 12 of stent 10 that are pressed into the wall of artery 16 will eventually be covered with endothelial cell growth that further minimizes blood flow turbulence. The serpentine pattern of cylindrical sections 12 provide good tacking characteristics to prevent stent movement within the artery. Furthermore, the closely spaced cylindrical elements 12 at regular intervals provide uniform support for the wall of artery 16, and consequently are well adapted to tack up and hold in place small flaps or dissections in the wall of artery 16 as illustrated in FIGS. 2 and 3.

In addition to the use of self-expandable stents, the stent designs of the present invention also can be used in conjunction with balloon expandable stents (not shown) made from stainless steel or other conventional stent materials. In such cases, the stent is mounted on an expandable member (balloon) and crimped tightly thereon so that the stent and expandable member present a low profile diameter for delivery through the arteries. The balloon is fully inflated with the stent expanded and pressed against the vessel wall, and the implanted stent remains in the vessel after the balloon has been deflated and the delivery catheter and guide wire have been withdrawn from the patient.

Figure 5:
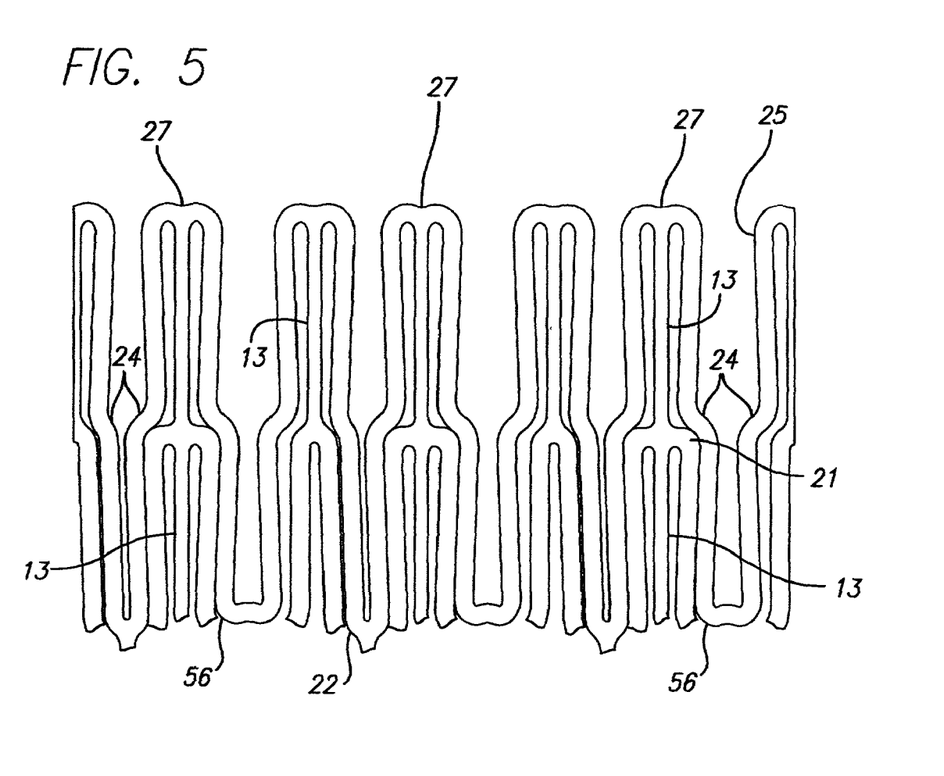
FIG. 5 is an enlarged partial view of the stent of FIG. 4 depicting the serpentine pattern along with the peaks and valleys which form one particular embodiment of a cylindrical element made in accordance with the present invention.
Figure 6:
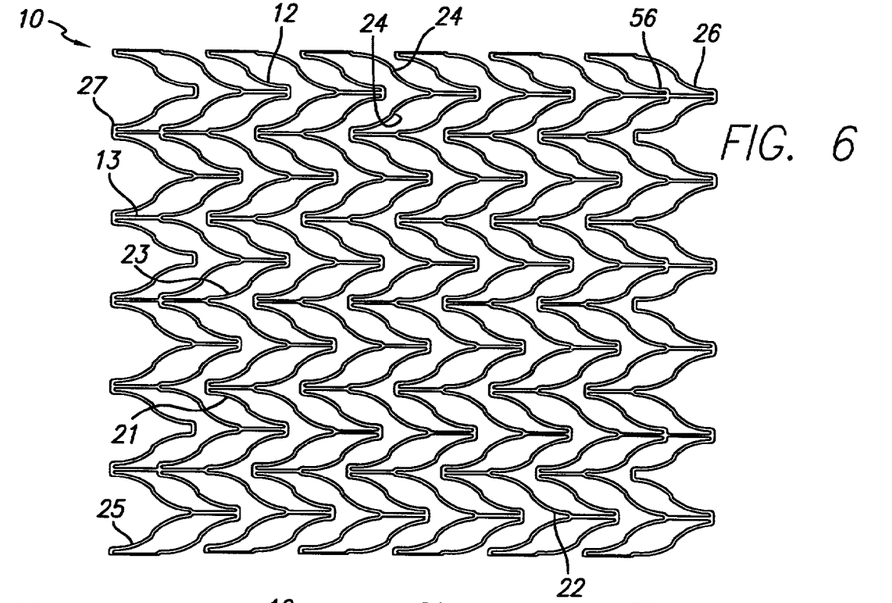
FIG. 6 is an enlarged plan view of the stent of FIG. 4 depicting the embodiment of the flattened stent of the present invention in an expanded condition.

The strains involved during expansion from a low profile to an expanded profile are generally evenly distributed among the various peaks and valleys of stent 10. Referring now to FIGS. 4-6, one embodiment of the present invention is shown wherein each expanded cylindrical element 12 embodies a serpentine pattern having a plurality of peaks and valleys that aid in the even distribution of expansion forces. In this exemplary embodiment, interconnecting members 13 serve to connect adjacent valleys of each adjacent cylindrical element 12 as described above. The valleys and peaks generally have a repeating pattern of Y, W and inverted Y, W shapes, respectively, to form each cylindrical element 12. It should be appreciated that the cylindrical element 12 can be formed in different shapes without departing from the spirit and scope of the present invention.

The cylindrical element 12 of this stent 10 includes double-curved portions (W) 21 located in the region of the valley where each interconnecting member 13 is connected to an adjacent cylindrical element 12. The peak portions (inverted Y) 22 and (inverted W) 56 and the valley portions (W's and Y's) 21 and 23 also form the cylindrical element 12 of the stent 10. A shoulder region 24 extending from each valley portion to peak portion (inverted Y) 22 and (inverted W) 56 allows the peak portion to be nested in a tight formation within an adjacent cylindrical element 12. This shoulder region 24 provides a transition region between the peak portions (inverted Y) 22 and (inverted W) 56 and the valley portions (Y) 23 and double-curved portion (W) 21 to allow adjacent cylindrical elements to nest within one another and thereby better support the artery walls with smaller gaps between stent struts. In this manner, the shoulder region 24 provides more dense coverage of the serpentine pattern of the cylindrical element to create a fairly uniform strut pattern which fully supports the walls of the diseased artery. For this reason, there are no or few areas of the stent wall which do not have struts for supporting the wall of the artery.

With further reference to FIGS. 4-6, each of the valley portions (W's and Y's) 21 and 23 have an interconnecting member which connects that cylindrical element 12 to an adjacent cylindrical element valley portion. Likewise, each of the peak portions (inverted W's and inverted Y's) 56 and 22 have an interconnecting member which connects that cylindrical element to an adjacent cylindrical element peak portion. Each cylindrical element 12 is connected to an adjacent cylindrical element by at least six interconnecting members 13. The placement of interconnecting members 13 within the body of the stent 10, particularly with respect to the interconnecting members that extend from the double-curved portions (W) 21 of each valley portion, is important to the stent design of the present invention. In particular, the specific placement of the interconnecting members that extend from the double-curved portions (W) of each valley portion help increase axial stiffness and reduce the protrusion of the Y's 23 from the circumference of the stent 10. The six interconnecting members 13 which are connected to each cylindrical element 12 are discontinuous with each other to produce a highly flexible stent that does not kink upon bending. This particular design allows the stent 10 to be placed in tortuous anatomy, where the stent 10 will conform to the particular anatomy of the patient. For example, if the stent 10 is placed in a curved portion of an artery, then the flexibility of the stent will allow it to take on the same curved shape without kinking and will still be capable of fully supporting the artery. Additionally, the stent's resistance to kinking helps prevent occlusion of the vessel lumen by the stent struts. Even though the stent 10 is flexible, it is still rigid when collapsed so that it can be placed on the delivery catheter and moved into the desired location in the patient's vasculature.

Referring to FIG. 5, the stent 10 also includes end rings 25 and 26 which include all W-shaped portions 27 to provide additional strength to the ends of the stent 10. The inclusion of the W pattern also helps to increase the overall radiopacity of the stent by virtue of the additional material needed to create such a W pattern. Accordingly, the stent 10 should be easily observable by a physician using imaging instrumentation, such as a fluoroscope.

As shown in FIG. 6, the stent 10 of the present invention is in an expanded condition which highlights the precise placement of the six interconnecting members within the body of the stent to help achieve the design objectives set forth above.

Figure 7:
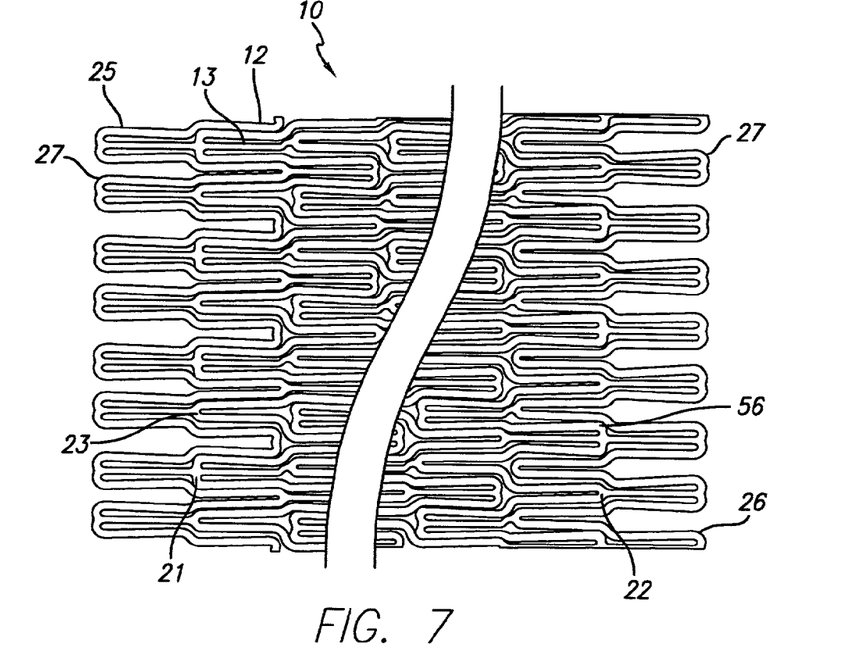
FIG. 7 is a plan view of an alternative embodiment of a flattened stent of the present invention, which illustrates the serpentine pattern including peaks and valleys which form the cylindrical elements of the stent and permit the stent to achieve a small crimp profile, yet is expandable to a larger diameter to maintain the patency of a small vessel.
Figure 8:
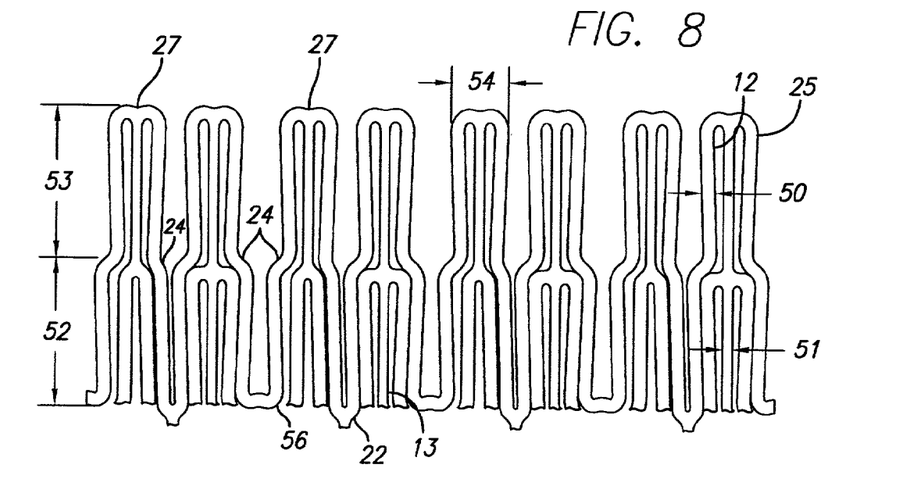
FIG. 8 is an enlarged partial view of the stent of FIG. 7 depicting the serpentine pattern along with the peaks and valleys which form another embodiment of a cylindrical element made in accordance with the present invention.
Figure 9:
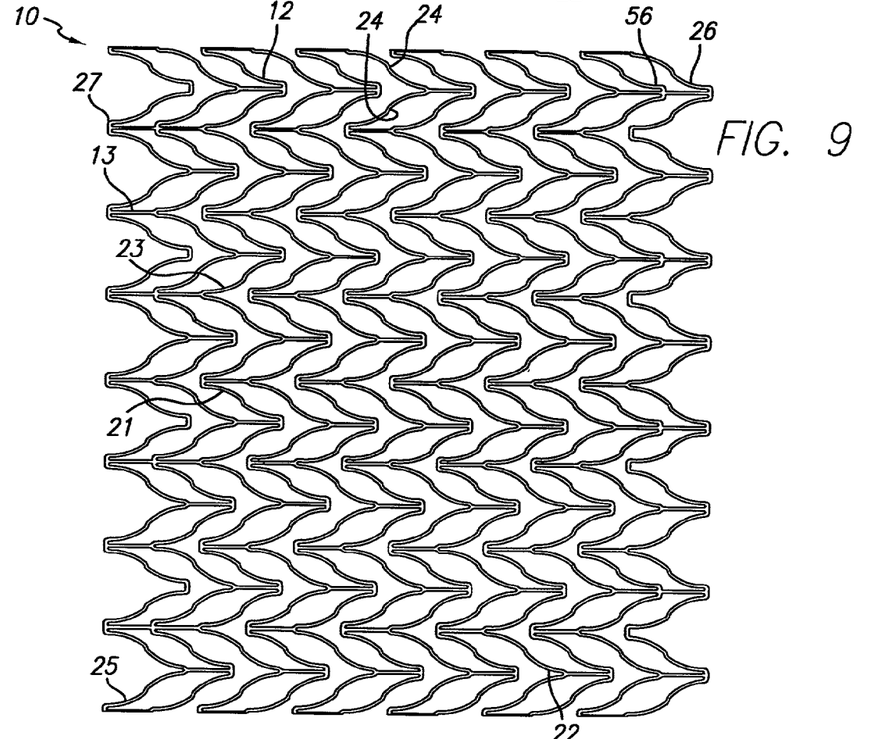
FIG. 9 is an enlarged plan view of the stent of FIG. 7 depicting the embodiment of the flattened stent of the present invention in an expanded condition.

In another embodiment of the present invention, as shown in FIGS. 7-9, the stent 10 is made with eight crowns or peak portions (inverted Y's and W's) 22, 56 rather than the six crowns shown in the previous embodiment. Otherwise, the strut pattern is virtually identical. The stent 10 includes eight valley portions, namely four double-curved (W) valley portions 21 and four Y-shaped valley portions 23. This particular design also has eight discontinuous interconnecting members 13 which connect each cylindrical element 12 to an adjacent cylindrical element. Again, the interconnecting members 13 extend from each of the double-curved (W) 21 valley portions and from each of the inverted, double-curved (W) 56 peak portions to help prevent shortening of the stent during radial expansion. This pattern also helps increase the flexibility of the strut. The design objectives of the stent of the present invention having certain physical properties as detailed for FIGS. 4-6 also apply to this embodiment. Namely, the specific placement of the interconnecting members extending from the double-curved portions (W) of each valley portion help increase axial stiffness and reduce the protrusion of the Y's 23 from the circumference of the stent 10. The W-shaped portions 27 which consist of end rings 25 and 26 provide additional strength to the ends of the stent 10 and help increase the radiopacity of the stent as well.

Figure 10:
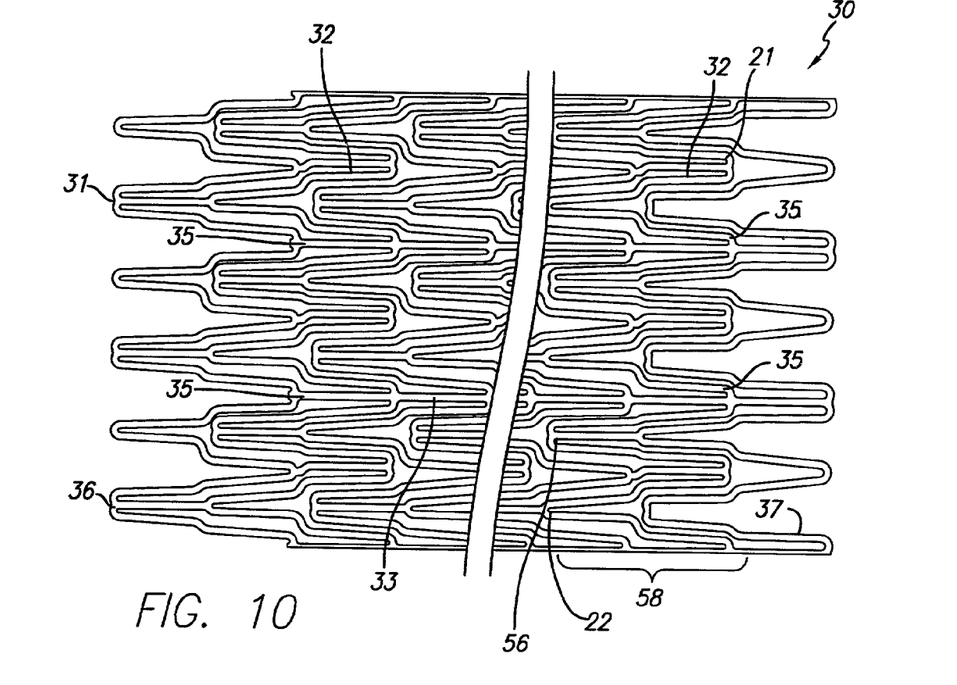
FIG. 10 is a plan view of an alternative embodiment of a flattened stent of the present invention, which illustrates the serpentine pattern along with the peaks and valleys which form the cylindrical elements of the stent and permit the stent to achieve a small crimp profile, yet is expandable to a larger diameter to maintain the patency of a small vessel.
Figure 11:
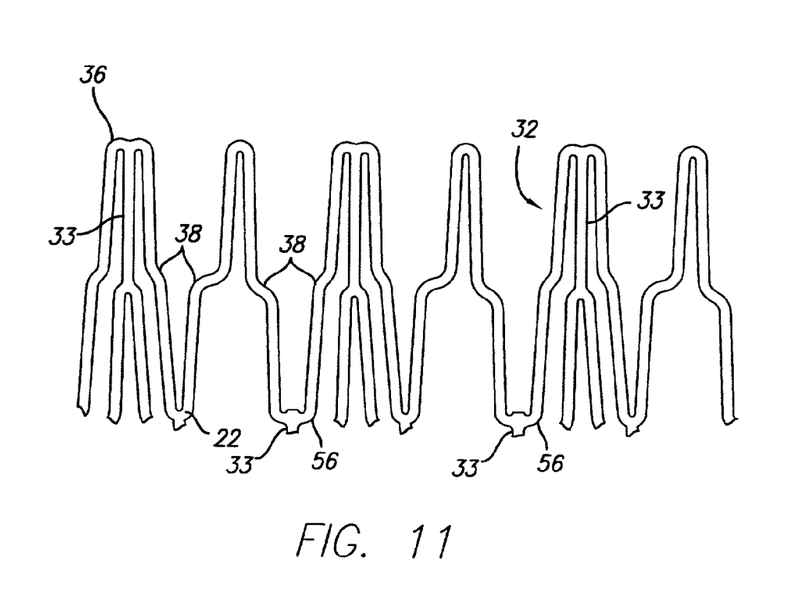
FIG. 11 is an enlarged partial view of the stent of FIG. 10 depicting the serpentine pattern along with the peaks and valleys which form another embodiment of a cylindrical element made in accordance with the present invention.

In another embodiment of the present invention, as shown in FIGS. 10 and 11, the stent 30 is made with cylindrical elements 32 having a pattern of a first set of cylindrical elements 58 alternate in a consecutive manner with the same pattern of a second set of cylindrical elements 58 throughout the body of the stent. The pattern consists of six valley portions, namely six double-curved portions 21, and six peak portions, namely three inverted double-curved portions 56 and three inverted Y-shaped portions 22. This particular design differs from the previous two embodiments by utilizing three continuous interconnecting members 33 to connect each of the cylindrical elements 32 to an adjacent cylindrical element. In this configuration, the serpentine pattern of each individual cylindrical element 32 is in phase with each other which helps reduce the contraction of the stent along each of its lengths upon expansion. The specific placement of the interconnecting members 33 extending from the double-curved portions (W) 21 and of each valley portion help increase axial stiffness and reduce the protrusion of the Y-shaped portions 23 from the circumference of the stent 10. Each interconnecting member 33 is connected to each double-curved portion (W) 21 and each inverted double-curved portion 56 of each cylindrical element. Further, with respect to the pattern of cylindrical elements 58, each interconnecting member 33 is connected to each inverted double-curved portion 56 such that the interconnecting members of each alternating, inverted double-curved portion form a continuous spine 35 which extends from one end 36 to the other end 37 of the stent 30. These continuous spines 35 help prevent the stent 30 from shortening when each of the cylindrical elements 32 are radially expanded.

The arrangement of the end rings 36 and 37 of the stent 30 differ from the previous embodiments in that each stent end includes three double-curved portions 21 and three Y-shaped portions 23 that alternate with each other in order to help increase the radial strength of both stent ends. Also, the cylindrical element 32 includes a shoulder region 38 which extends between each of the valley portions and peak portions to provide a transition region which allows the inverted Y-shaped peak portion 22 to be crimped in close proximity to an adjacent cylindrical element. In this manner, the stent 30 can be crimped down to a low profile which helps reduce the overall profile of the stent and delivery catheter when placing the stent 30 through the tortuous anatomy of the patient's vasculature.

Figure 12:
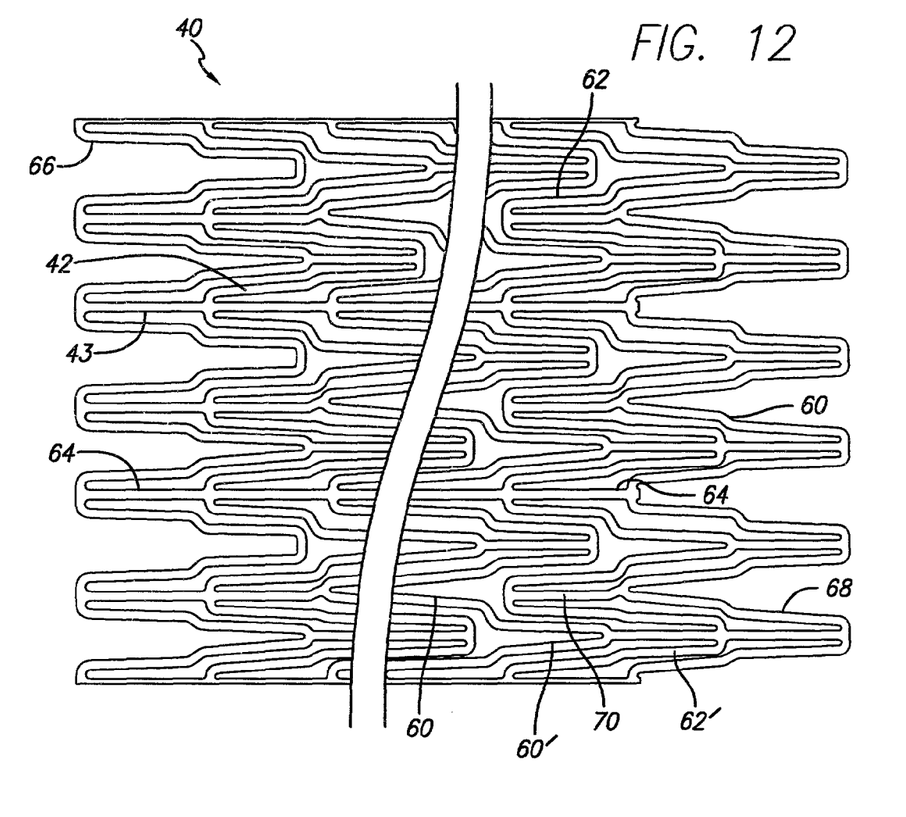
FIG. 12 is a plan view of an alternative embodiment of a flattened stent of the present invention, which illustrates the serpentine pattern along with the peaks and valleys which form the cylindrical elements of the stent and permit the stent to achieve a small crimp profile, yet is expandable to a larger diameter to maintain the patency of a small vessel.
Figure 13:
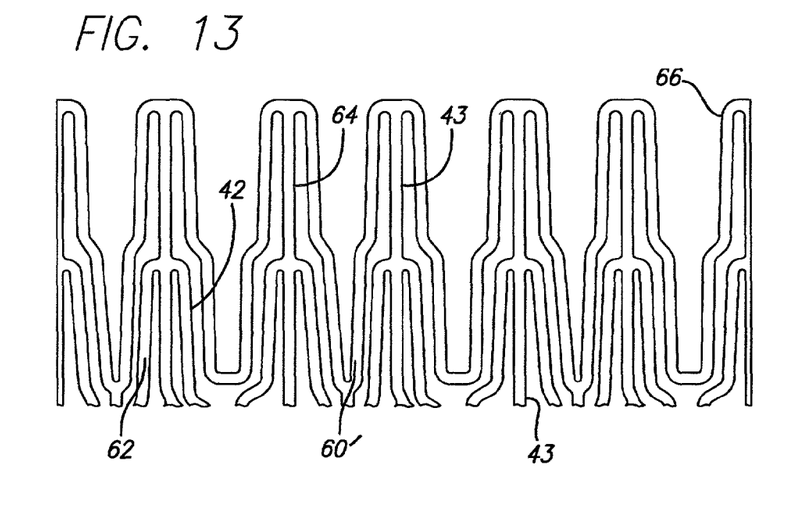
FIG. 13 is an enlarged partial view of the stent of FIG. 12 depicting the serpentine pattern along with the peaks and valleys which form another embodiment of a cylindrical element made in accordance with the present invention.

In yet another embodiment of the present invention, as shown in FIGS. 12 and 13, a stent 40 is shown having a plurality of cylindrical elements 42 which are connected together by interconnecting members 43. Each of the cylindrical elements 42 include six peak portions, namely three inverted Y-shaped portions 60' and three inverted double-curved portions 62', and six valley portions, namely three Y-shaped portions 60 and three double-curved portions 62. This particular embodiment of stent 40 differs from the previous embodiments in that the W-shaped portions of each cylindrical element 42 are aligned in such a manner that forms a continuous spine 64 extending from one end 66 of the stent to the other 68. Further, the end rings 66 and 68 of this particular stent 40 include six double-curved portions 62 which helps increase the radial strength of this end while enhancing radiopacity as well.

In all of the embodiments disclosed herein (FIGS. 4-13), alternating spines 70 are created throughout the body of the stent due to the precise placement of the interconnecting members 13/33/43 in connecting adjacent cylindrical elements 12/32/42 to each other.

It should be appreciated that the present design can be made with a number of peaks and valleys ranging from four to sixteen. The number of peaks and valleys will depend upon the particular physical characteristics desired, along with the particular application to which the stent will be used.

For ease of illustration, the present invention is depicted in a flattened plan view in most of the drawing figures herein. It should be noted, however, that all of the embodiments depicted herein are cylindrically-shaped stents that are generally formed from tubing by laser cutting as described below.

One important feature of all of the embodiments of the present invention is the capability of the stents to expand from a low-profile diameter to a larger diameter, while still maintaining structural integrity in the expanded condition and remaining highly flexible. Stents of the present invention each have an overall expansion ratio of about 1.0 up to about 7.0 times the original diameter, or more, using certain compositions of materials. The stents still retain structural integrity in the expanded condition and will serve to hold open the vessel in which they are implanted. Some materials may afford higher or lower expansion ratios without sacrificing structural integrity.

While the stent design of the present invention has very practical applications for procedures involving vessel diameters from about 3.0 to 26.0 millimeters, it should be appreciated that the stent pattern could also be successfully used in procedures involving larger lumens of the body, without departure from the spirit and scope of the present invention. Due to the increase of the longitudinal flexibility provided by the present stent design, such applications could include larger diameter vessels where added flexibility in reaching the vessel is needed.

The aforedescribed illustrative stent of the present invention, including its various embodiments, and similar stent structures can be made in many ways. One method of making the stent, however, is to cut a thin-walled tubular member, such as Nitinol tubing, and remove portions of the tubing in the desired pattern for the stent, leaving relatively untouched the portions of the metallic tubing which are to form the stent. The tubing can be cut in the desired pattern by means of a machine-controlled laser.

A suitable composition of Nitinol used in the manufacture of a self-expanding stent of the present invention is approximately 55% nickel and 44.5% titanium (by weight) with trace amounts of other elements making up about 0.5% of the composition. The austenite transformation temperature is between about −15° C. and 30° C. in order to achieve superelasticity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of Nitinol can be utilized, as can other self-expanding alloys, to obtain the same features of a self-expanding stent made in accordance with the present invention. Further details of how NiTi superelastic alloys operate can be found in U.S. Pat. No. 4,665,906 (Jervis) and U.S. Pat. No. 5,067,957 (Jervis).

The stent of the present invention can be laser cut from a tube of superelastic (sometimes called pseudoelastic) nickel titanium (Nitinol) whose transformation temperature is below body temperature. All of the stent diameters can be cut with the same stent pattern, and the stent is expanded and heat treated to be stable at the desired final diameter. The heat treatment also controls the transformation temperature of the Nitinol such that the stent is superelastic at body temperature. The transformation temperature is at or below body temperature so that the stent will be superelastic at body temperature. The stent can be electropolished to obtain a smooth finish with a thin layer of titanium oxide placed on the surface. The stent is usually implanted into the target vessel which is smaller than the stent diameter so that the stent applies a force to the vessel wall to keep it open.

The stent tubing of a stent made in accordance with the present invention may be made of suitable biocompatible material besides superelastic nickel-titanium (NiTi) alloys. In this case, the stent would be formed using known techniques for manufacturing balloon expandable stents. The tubing may be made, for example, a suitable biocompatible material such as stainless steel. The stainless steel tube may be alloy-type: 316L SS, Special Chemistry per ASTM F138-92 or ASTM F139-92 grade 2.

The stent diameters are very small, so the tubing from which it is made must necessarily also have a small diameter. For PTCA applications, typically the stent has an outer diameter on the order of about 1 millimeter (0.04-0.09 inches) in the unexpanded condition, the same outer diameter of the hypotubing from which it is made, and can be expanded to an outer diameter of 4.0 millimeter or more. The wall thickness of the tubing is about 0.076-0.381 millimeter (0.003-0.015 inches). For stents implanted in other body lumens, such as PTA applications, the dimensions of the tubing are correspondingly larger. While it is preferred that the stents be made from laser cut tubing, those skilled in the art will realize that the stent can be laser cut from a flat sheet and then rolled up in a cylindrical configuration with the longitudinal edges welded to form a cylindrical member.

Referring now to FIG. 8, the width of the strut of the cylindrical element, indicated by arrows 50, can be about from 0.003 to 0.009 inches. The width of the strut of the interconnecting member, indicated by arrows 51, can be from about 0.003 to 0.009 inches. The length from the double-curved portion to the shoulder region, indicated by arrow 52, can be from about 0.05 to 0.25 inches. The length from the shoulder region to the top of the peak portion, indicated by arrow 53, can be from about 0.05 to 0.25 inches. The width of the peak portions (unexpanded) indicated by arrows 54, can be from about 0.012 to 0.060 inches. These same dimensions also apply to all of the other embodiments of the present invention disclosed herein.

Due to the thin wall and the small geometry of the stent pattern, it is necessary to have very precise control of the laser, its power level, the focus spot size, and the precise positioning of the laser cutting path. In cutting the strut widths of the embodiments disclosed herein, it is preferable to have a very focused laser spot size which will allow the precise strut pattern to be created on the tubing. For this reason, additional instrumentation which includes a series of lenses may be necessary to be utilized with the laser in order to create the fine focused laser spot necessary to cut that particular pattern.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished stent. Further details on how the tubing can be cut by a laser are found in U.S. Pat. No. 5,759,192 (Saunders), U.S. Pat. No. 5,780,807 (Saunders) and U.S. Pat. No. 6,131,266 (Saunders), which have been assigned to Advanced Cardiovascular Systems, Inc.

The process of cutting a pattern for the stent into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

After the stent has been cut by the laser, electrical chemical polishing, using various techniques known in the art, should be employed in order to create the desired final polished finish for the stent. The electropolishing will also be able to take off protruding edges and rough surfaces which were created during the laser cutting procedure.

While the invention has been illustrated and described herein in terms of its use as intravascular stents, it will be apparent to those skilled in the art that the stents can be used in other instances in all conduits in the body, such as, but not limited to, the urethra and esophagus. Other modifications and improvements may be made without departing from the scope of the invention.

What is claimed:

1. A longitudinally flexible stent for implanting in a body lumen and expandable from a contracted condition to an expanded condition, comprising:

a plurality of adjacent cylindrical elements, each cylindrical element having a circumference extending about a longitudinal stent axis and being substantially independently expandable in the radial direction;

wherein the plurality of adjacent cylindrical elements are arranged in alignment along the longitudinal stent axis and form a generally serpentine wave pattern transverse to the longitudinal axis and each cylindrical element has a plurality of alternating valley portions and peak portions, the valley portions including alternating double-curved portions and Y-shaped portions, and the peak portions including alternating, inverted double-curved portions and inverted Y-shaped portions; and a plurality of interconnecting members extending between the adjacent cylindrical elements and connecting the adjacent cylindrical elements to one another, interconnecting members being connected to the alternating double-curved portions to connect a cylindrical element to the Y-shaped portion of an adjacent cylindrical element, and interconnecting members being connected to the alternating, inverted double-curved portion to connect a cylindrical element to the alternating, inverted Y-shaped portion of an adjacent cylindrical element.

2. The stent of claim 1, further including shoulder regions interconnecting the valley portions and peak portions.

3. The stent of claim 2, wherein the double-curved portions have a reduced profile to allow the shoulder regions to collapse closer to each double-curved portion.

4. The stent of claim 1, wherein each cylindrical element includes approximately four to sixteen alternating peak portions and valley portions.

5. The stent of claim 4, wherein interconnecting members are attached to each of the alternating double-curved portions and alternating, inverted double-curved portions of each cylindrical element.

6. The stent of claim 5, further including shoulder regions interconnecting the valley portions and peak portions.

7. The stent of claim 6, wherein the shoulder regions provide a transition region between the valley portion and peak portions which allow the peak portions to have a narrower width.

8. The stent of claim 1, wherein the plurality of interconnecting members are aligned end to end.

9. The stent of claim 1, wherein the stent is formed from a flat piece of material.

10. The stent of claim 1, wherein the stent is formed from a piece of tubing.

11. The stent of claim 1, wherein the stent is made from a pseudoelastic alloy material.

12. The stent of claim 1, wherein the stent includes a shape memory alloy material.

13. The stent of claim 1, wherein the stent is formed from a biocompatible material selected from the group consisting of stainless steel, tungsten, tantalum, superelastic nickel titanium alloys, and thermal plastic polymers.

14. The stent of claim 1, wherein each cylindrical element includes eight alternating peak portions and eight valley portions.

15. The stent of claim 14, wherein the eight alternating valley portions comprise of four double-curved portions and four Y-shaped portions.

16. The stent of claim 15, further including cylindrical elements located at both ends of the stent which have a pattern of double-curved portions on one end and a pattern of inverted double-curved portions on the opposite end of the stent.

17. The stent of claim 14, wherein the eight alternating peak portions comprise of four inverted double-curved portions and four inverted Y-shaped portions.

18. The stent of claim 14, wherein eight interconnecting members are attached to each of the alternating double-curved portions and alternating, inverted double-curved portions of each cylindrical element.

19. The stent of claim 1, wherein each cylindrical element includes six alternating peak portions and six valley portions.

20. The stent of claim 19, wherein the six alternating valley portions comprise of three double-curved portions and three Y-shaped portions.

21. The stent of claim 20, wherein six interconnecting members are attached to each of the alternating double-curved portions and alternating, inverted double-curved portions of each cylindrical element.

22. The stent of claim 21, further including shoulder regions interconnecting the valley portions and peak portions.

23. The stent of claim 19, wherein the six alternating peak portions comprise of three inverted double-curved portions and three inverted Y-shaped portions.

24. The stent of claim 20, further including cylindrical elements located at both ends of the stent which have a pattern of double-curved portions on one end and a pattern of inverted double-curved portions on the opposite end of the stent.

25. The stent of claim 1, further including cylindrical elements located at the ends of the stent which have a pattern of double-curved portions on one end and a pattern of inverted double-curved portions on the opposite end of the stent.

26. The stent of claim 1, wherein the stent is made from a self-expanding material.

27. A longitudinally flexible stent for implanting in a body lumen and expandable from a contracted condition to an expanded condition, comprising:
  a plurality of adjacent cylindrical elements, each cylindrical element having a circumference extending about a longitudinal stent axis and being substantially independently expandable in the radial direction;
  wherein the plurality of adjacent cylindrical elements are arranged in alignment along the longitudinal stent axis and form a generally serpentine wave pattern transverse to the longitudinal axis containing a plurality of alternating valley portions and peak portions;
  the plurality of adjacent cylindrical elements alternate between a pattern of double-curved portions, inverted double-curved portions, and inverted Y-shaped portions, to form the body of the stent; and
  a plurality of interconnecting members extending between the adjacent cylindrical elements and connecting adjacent cylindrical elements to one another, interconnecting members of each alternating, inverted double-curved portion within each cylindrical element forming a continuous spine extending from one end of the stent to the other.

28. The stent of claim 27, wherein the pattern includes six peak portions and six valley portions.

29. The stent of claim 28, wherein the six peak portions comprise of three inverted double-curved portions and three inverted Y-shaped portions.

30. The stent of claim 28, wherein the six valley portions comprise of six double-curved portions.

31. The stent of claim 27, wherein each of the cylindrical elements are connected to an adjacent cylindrical element by three interconnecting members.

32. The stent of claim 27, further including cylindrical elements located at both ends of the stent which have an alternating pattern of inverted double-curved portions and Y-shaped portions on one end and a pattern of alternating double-curved portions and inverted Y-shaped portions on the opposite end of the stent.

33. The stent of claim 27, wherein the stent is made from a self-expanding material.

34. A longitudinally flexible stent for implanting in a body lumen and expandable from a contracted condition to an expanded condition, comprising:
  a plurality of adjacent cylindrical elements, each cylindrical element having a circumference extending about a longitudinal stent axis and being substantially independently expandable in the radial direction;
  wherein the plurality of adjacent cylindrical elements are arranged in alignment along the longitudinal stent axis and form a generally serpentine wave pattern transverse to the longitudinal axis containing a plurality of alternating valley portions and peak portions, the valley portions including alternating Y-shaped portions and double-curved portions, and the peak portions including alternating, inverted Y-shaped portions and inverted double-curved portions; and
  a plurality of interconnecting members extending between the adjacent cylindrical elements and connecting adjacent cylindrical elements to one another, interconnecting members of each double-curved portion within each cylindrical element forming a continuous spine extending from one end of the stent to the other.

35. The stent of claim 34, wherein each of the cylindrical elements include six peak portions and six valley portions.

36. The stent of claim 35, wherein the six peak portions comprise of three inverted Y-shaped portions and three inverted double-curved portions.

37. The stent of claim 35, wherein the six valley portions comprise of three Y-shaped portions and three double-curved portions.

38. The stent of claim 34, wherein further including cylindrical elements located at both ends of the stent which have a pattern of alternating, inverted double-curved portions and Y-shaped portions on one end and a pattern of alternating double-curved and inverted Y-shaped portions on the opposite end of the stent.

39. The stent of claim 34, wherein the stent is made from a self-expanding material.

40. A method of making a longitudinally flexible stent for implanting in a body lumen and expandable from a contracted condition to an expanded condition, the method comprising the steps of:
provide a plurality of adjacent cylindrical elements, wherein each cylindrical element has a circumference extending around a longitudinal stent axis and is substantially independently expandable in the radial direction;
arranging the plurality of adjacent cylindrical elements in alignment along the longitudinal stent axis;
forming a serpentine wave pattern transverse to the longitudinal axis containing a plurality of alternating valley portions and peak portions on each of the cylindrical elements, the valley portions including alternating double-curved portions and Y-shaped portions and the peak portions including alternating, inverted double-curved portions and inverted Y-shaped portions;
providing a plurality of interconnecting members extending between the adjacent cylindrical elements; and
connecting the adjacent cylindrical elements to one another, interconnecting members being connected to the double-curved portions to connect a cylindrical element to the Y-shaped portion of an adjacent cylindrical element and interconnecting members being connected to the alternating, inverted double-curved portion to connect the cylindrical element to the alternating, inverted Y-shaped portion of an adjacent cylindrical element.

41. The method of claim 40, wherein the step of forming the serpentine wave pattern further comprises nesting the double-curved and Y-shaped valley portions of one cylindrical element within an adjacent cylindrical element by arranging the serpentine patterns in phase with each other.

42. The method of claim 40, wherein the step of providing a plurality of adjacent cylindrical elements includes forming the cylindrical elements from shape memory alloy material.

43. The method of claim 40, wherein the step of providing a plurality of adjacent cylindrical elements includes forming the cylindrical elements from a pseudoelastic alloy material.

44. The method of claim 40, wherein the step of connecting the adjacent cylindrical elements to one another further includes having cylindrical elements located at both ends of the stent which have an alternating pattern of inverted double-curved portions and Y-shaped portions on one end and a pattern of alternating double-curved portions and inverted Y-shaped portions on the opposite end of the stent.

45. The method of claim 40, wherein the step of connecting the adjacent cylindrical elements to one another further includes having cylindrical elements located at the ends of the stent which have a pattern of double-curved portions on one end and a pattern of inverted double-curved portions on the opposite end of the stent.

46. A longitudinally flexible stent for implanting in a body lumen and expandable from a contracted condition to an expanded condition, comprising:
a plurality of adjacent cylindrical elements, each cylindrical element having a circumference extending about a longitudinal stent axis and being substantially independently expandable in the radial direction;
wherein the plurality of adjacent cylindrical elements are arranged in alignment along the longitudinal stent axis and form a generally serpentine wave pattern transverse to the longitudinal axis and each cylindrical element has a plurality of alternating valley portions and peak portions, the valley portions including alternating double-curved portions and Y-shaped portions and the peak portions including alternating, inverted double-curved portions and inverted Y-shaped portions; and
a plurality of interconnecting members extending between the adjacent cylindrical elements and connecting the adjacent cylindrical elements to one another.

47. The stent of claim 46, wherein some interconnecting members connect the inverted double-curved portions of one cylindrical element to the inverted Y-shaped portions of an adjacent cylindrical element.

48. The stent of claim 46, wherein some interconnecting members connect the double-curved portions of one cylindrical element to the Y-shaped portions of an adjacent cylindrical element.

49. The stent of claim 46, wherein some interconnecting members connect the inverted double-curved portions of one cylindrical element to the inverted Y-shaped portions of an adjacent cylindrical element and some interconnecting members connect the double-curved portions of one cylindrical element to the Y-shaped portions of an adjacent cylindrical element.

50. The stent of claim 46, further including shoulder regions interconnecting the valley portions and peak portions.

51. The stent of claim 46, further including cylindrical elements located at the ends of the stent which have a pattern of double-curved portions on one end and a pattern of inverted double-curved portions on the opposite end of the stent.

52. The stent of claim 46, wherein the stent is made from a self-expanding material.

* * * * *